US010307443B2

(12) United States Patent
Spencer et al.

(10) Patent No.: US 10,307,443 B2
(45) Date of Patent: *Jun. 4, 2019

(54) MICRONIZED WHARTON'S JELLY

(71) Applicant: MiMedx Group, Inc., Marietta, GA (US)

(72) Inventors: Randall Spencer, Marietta, GA (US); Somaly Sith, Marietta, GA (US); Tom Koob, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/166,016

(22) Filed: May 26, 2016

(65) Prior Publication Data

US 2016/0346332 A1    Dec. 1, 2016

Related U.S. Application Data

(63) Continuation of application No. 14/793,673, filed on Jul. 7, 2015, now abandoned.

(60) Provisional application No. 62/022,084, filed on Jul. 8, 2014.

(51) Int. Cl.
| | |
|---|---|
| *A61K 35/51* | (2015.01) |
| *A61K 9/00* | (2006.01) |
| *A61K 9/16* | (2006.01) |
| *A61K 9/14* | (2006.01) |
| *C12N 5/078* | (2010.01) |

(52) U.S. Cl.
CPC ............ *A61K 35/51* (2013.01); *A61K 9/0019* (2013.01); *A61K 9/14* (2013.01); *A61K 9/16* (2013.01); *C12N 5/065* (2013.01); *C12N 2509/10* (2013.01)

(58) Field of Classification Search
CPC .............. A61K 35/51; A61K 9/14; A61K 9/16
See application file for complete search history.

(56) References Cited

U.S. PATENT DOCUMENTS

| 4,378,025 | A | | 3/1983 | Gaston |
| 5,206,023 | A | * | 4/1993 | Hunziker ............ A61L 24/0015 |
| | | | | 424/422 |
| 5,558,071 | A | | 9/1996 | Ward et al. |
| 5,639,796 | A | * | 6/1997 | Lee ...................... A61K 9/0024 |
| | | | | 424/423 |
| 5,919,702 | A | * | 7/1999 | Purchio ............... A61L 27/3633 |
| | | | | 424/93.1 |
| 6,579,851 | B2 | | 6/2003 | Goeke et al. |
| 8,067,044 | B2 | | 11/2011 | Henry et al. |
| 8,071,135 | B2 | | 12/2011 | Liu et al. |
| 8,105,634 | B2 | | 1/2012 | Liu et al. |
| 8,357,403 | B2 | | 1/2013 | Daniel et al. |
| 8,372,437 | B2 | | 2/2013 | Daniel |
| 8,460,715 | B2 | | 6/2013 | Daniel |
| 8,461,129 | B2 | | 6/2013 | Bolduc et al. |
| 8,904,664 | B2 | | 12/2014 | Pringle et al. |
| 9,005,646 | B2 | | 4/2015 | Masinaei et al. |
| 2010/0209408 | A1 | * | 8/2010 | Stephen ................ A61K 35/32 |
| | | | | 424/93.71 |
| 2012/0141595 | A1 | | 6/2012 | Tseng et al. |
| 2013/0041004 | A1 | | 2/2013 | Drager et al. |
| 2013/0096073 | A1 | | 4/2013 | Sidelman |
| 2013/0344162 | A1 | | 12/2013 | Morse et al. |
| 2014/0017280 | A1 | | 1/2014 | Daniel et al. |
| 2014/0050788 | A1 | | 2/2014 | Daniel et al. |
| 2014/0052247 | A1 | | 2/2014 | Daniel et al. |
| 2014/0052274 | A1 | | 2/2014 | Koob et al. |
| 2014/0067058 | A1 | | 3/2014 | Koob et al. |
| 2014/0106447 | A1 | | 4/2014 | Brown et al. |

(Continued)

FOREIGN PATENT DOCUMENTS

| CN | 102198292 A | 9/2011 |
| WO | WO-2012/112410 A2 | 8/2012 |

(Continued)

OTHER PUBLICATIONS

Diaz-Prado, S. et al. "Potential use of the human amniotic membrane as a scaffold in human articular cartilage repair" Cell Tissue Bank (2010) 11:183-195.*
OrthoInfo (http://orthoinfo.aaos.org/topic.cfm?topic=a00422) Feb. 2009, pp. 1-5.*
Autogeneous definition (http://medical-dictionary.thefreedictionary.com/autogenous) accessed Mar. 8, 2017, p. 1-2.*
Diaz-Prado, S. et al. "Potential use of the human amniotic membrane as a scaffold in human articular cartilage repair". Cell Tissue Bank (2010) 11:183-195 (Year: 2010).*
OrthoInfo (http://orthoinfo.aaos.org/topic.cfm?topic=a00422) Feb. 2009, pp. 1-5 (Year: 2009).*
Autogeneous definition (http://medical-dictionary.thefreedictionary.com/autogenous) accessed Mar. 8, 2017, p. 1-2. (Year: 2017).*
Wharton's Jelly definition (http://rnedical-dictionary.thefreedictionary.com/Wharton's+jelly) accessed Dec. 10, 2015, p. 1-2 (Year: 2015).*

(Continued)

*Primary Examiner* — Andrew S Rosenthal
(74) *Attorney, Agent, or Firm* — Alston & Bird LLP

(57) ABSTRACT

The present invention provides compositions and formulations of micronized Wharton's jelly having a controlled viscosity such that when delivered to the injured region of a subject, it remains substantially localized with little or no migration out of the injured region for the repair and/or regeneration thereof. Micronized Wharton's Jelly can be suspended in a pharmaceutically acceptable aqueous carrier, such as saline, sterile water, or any suitable buffer, to form a suspension or a gelatinous gel composition, or it can be in the form of a paste, suitable for delivery into the space adjacent the articular surface cartilage injured region of a subject. The micronized Wharton's jelly when employed at sufficient concentrations can be hydrated into a gel or paste and administered topically, or it can be injected into the body through the use of a needle and syringe. Accordingly, micronized Wharton's Jelly, compositions, or formulations thereof, can be delivered in a manner that is more convenient than Wharton's jelly that has not been micronized in accordance with the present invention.

22 Claims, No Drawings

(56) References Cited

U.S. PATENT DOCUMENTS

| | | |
|---|---|---|
| 2014/0112998 A1 | 4/2014 | Tseng et al. |
| 2014/0255496 A1 | 9/2014 | Daniel et al. |
| 2014/0255508 A1 | 9/2014 | Morse et al. |
| 2014/0302162 A1 | 10/2014 | Morse et al. |
| 2015/0064274 A1 | 3/2015 | Koob |
| 2015/0250829 A1 | 9/2015 | Daniel et al. |
| 2016/0000968 A1 | 1/2016 | Koob et al. |

FOREIGN PATENT DOCUMENTS

| | | | |
|---|---|---|---|
| WO | WO 2013016444 A2 * | 1/2013 | ............ C08K 5/1539 |
| WO | WO-2013016444 A2 * | 1/2013 | ............ C08K 5/1539 |
| WO | WO-2013/102219 A1 | 7/2013 | |
| WO | WO-2015/179711 A1 | 11/2015 | |

OTHER PUBLICATIONS

Ahmed, A.U. "An overview of inflammation: mechanism and consequences" Front. Biol. 2011, 6(4): 274-281.

Amnion definition (http://medical-dictionary.thefreedictionary.com/amnion) accessed Dec. 10, 2015.

Amniotic membrane definition (http://medical-dictionary.thefreedictionary.com/Amniotic membrane) accessed Dec. 10, 2015.

Gogiel et al., "Proteoglycans of Wharton's jelly", Int'l J Biochem & Cell Bio, 2003, 35:1461-1469.

Liu et al. "A preliminary evaluation of efficacy and safety of Wharton's jelly mesenchymal stem cell transplantation in patients with type 2 diabetes mellitus" Stem Cell Research & Therapy 2014, 5:57, 1-9.

PCT International Search Report and Written Opinion dated Aug. 5, 2015 for PCT/US15/32078 16 pages.

PCT International Search Report and Written Opinion for PCT Application No. PCT/US15/39444 dated Sep. 30, 2015.

Purion Processed Dehydrated Human Amnion/Chlorion Membrane Allografts, 2012, http://www.iopinc.com/wpcontent/uploades/2012/05/Ambio_AM_Process_Monograph-May-12.pdf.

Wharton's Jelly definition (http://medical-dictionary.thefreedictionary.com/Wharton's jelly) accessed Dec. 10, 2015.

Stocco, E., et al., "Tailored PVA/ECM Scaffolds for Cartilage Regeneration," BioMed Research International, 2014, pp. 1-12, vol. 2014.

Supplemental European Search Report dated Oct. 26, 2017 for related European Patent Application No. 15819525.5.

Schillinger, M., et al., "Restenosis after percutaneous angioplasty: the role of vascular inflammation," Vascular Health Risk Management, Mar. 2005, vol. 1, No. 1, pp. 73-78.

Office Action for European Application No. 15819525.5 dated Dec. 6, 2018.

\* cited by examiner

MICRONIZED WHARTON'S JELLY

CROSS REFERENCE TO RELATED APPLICATIONS

This application is a continuation application of U.S. patent application Ser. No. 14/793,673, filed Jul. 7, 2015, which claims the benefit of U.S. Provisional Application Ser. No. 62/022,084, filed Jul. 8, 2014, the entireties of which are incorporated herein by reference.

FIELD OF THE INVENTION

The present invention is directed to micronized Wharton's jelly, compositions and formulations comprising the micronized Wharton's jelly, and methods of using micronized Wharton's jelly and compositions and formulations thereof.

BACKGROUND OF THE INVENTION

Articular surface defects include injuries as a result of sport related trauma, impact injury or a past injury persisting for prolonged time periods. The acute and repetitive impact and torsional joint loading that occurs, for example, during participation in sports can damage articular surfaces causing pain, joint dysfunction, and effusions. In some instances, this particular surface damage leads to progressive joint degeneration and osteoarthritis of the joint. In most instances, joints can repair damage that does not disrupt the articular surface if they are protected from additional injury. Mechanical disruption of articular cartilage stimulates chondrocyte synthetic activity, but it rarely results in repair of the injury. Disruption of subchondral bone stimulates chondral and bony repair, but it rarely restores an articular surface that duplicates the biologic and mechanical properties of normal articular cartilage. Articular surface defects are difficult to heal or regenerate spontaneously.

Wharton's jelly is a viscous gelatinous substance found in the umbilical cord of mammals (hereinafter referred to as 'Native Wharton's Jelly'). Native Wharton's Jelly contains high amounts of host extracellular matrix (ECM) components (including chondroitin sulfate, collagen, hyaluronic acid (HA), proteoglycans, and stem cells. Native Wharton's Jelly may also include growth factors such as, for example, fibroblast growth factor (FGF), insulin-like growth factor I (IGF-I), transforming growth factor beta (TGF-beta), platelet-derived growth factor (PDGF) and epidermal growth factor (EGF). Native Wharton's Jelly also has a significant elasticity characteristic as well as binding of water molecules.

In particular surface defects, the approach in addressing this condition is one of "repair or regeneration". "Repair" refers to healing of the injured tissue or replacement by cell proliferation and new ECM. "Regeneration" refers to formation of entirely new articular surface which is identical to the original tissue. Key growth factors which can chemotactically cause cell proliferation, deliver ECM and cellular differentiation to hyaline cartilage are introduced to aid repair or regeneration.

While Native Wharton's Jelly is contemplated to provide essential elements for both the repair and regeneration of articular surface cartilage, it is a viscous gelatin that is difficult to deliver into the body for repair and/or regeneration. Accordingly, there is a need to provide Native Wharton's Jelly that can be readily and reliably delivered to the injured region of a subject for repair and/or regeneration of the articular surface cartilage thereof.

SUMMARY OF THE INVENTION

In one aspect, the present invention provides compositions and formulations of micronized Native Wharton's Jelly having a controlled viscosity such that when delivered to the injured region of a subject, it remains substantially localized with little or no migration out of the injured region for the repair and/or regeneration thereof. In some embodiments, micronized Native Wharton's Jelly according to the present invention can be suspended in a pharmaceutically acceptable aqueous carrier, such as saline, sterile water, or any suitable buffer known in the art, to form a suspension or a gelatinous gel composition, or it can be in the form of a paste, suitable for delivery into the space adjacent the articular surface cartilage injured region of a subject as described herein. As such, the micronized Native Wharton's Jelly in accordance with the present invention is versatile because when employed at sufficient concentrations, it can be hydrated into a gel or paste and administered topically, or it can be injected into the body through the use of a needle and syringe. In at least these respects, micronized Native Wharton's Jelly, compositions, or formulations thereof, can be delivered in a manner that is more convenient than Native Wharton's jelly that has not been micronized in accordance with the present invention.

DETAILED DESCRIPTION OF THE INVENTION

It is to be understood that the aspects of the present invention as described below are not limited to specific compositions, methods or preparing such compositions, or uses thereof, as such may, of course, vary. It is also to be understood that the terminology used herein is for the purpose of describing particular aspects only and is not intended to be limiting.

As set forth in the specification and in the appended claims that follow, reference will be made to a number of terms that shall be defined to have the following meanings:

As used in the specification and the appended claims, the singular forms "a", "an" and "the" include plural referents unless the context clearly dictates otherwise. Thus, for example, reference to "a bioactive agent" includes a single bioactive agent and mixtures of two or more bioactive agents, and the like.

The term "Optional" or "optionally" means that the subsequently described event or circumstance can or may occur, or cannot or may not occur, and that the description includes instances where the event or circumstance occurs and instances where it does not. For example, the phrase "optionally cleaning step" means that the cleaning step may or may not be performed.

The term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of the present invention.

The term "subject" or "patient" as used herein means any vertebrate organism including but not limited to mammalian subjects such as humans, domestic animals such as cows, pigs, horses, dogs, cats, rabbits, rats and mice, and non-domesticated animals.

The term "placental tissue" means any and all of the well-known components of the placenta including but not limited to amnion, chorion, and the like, and including processed tissue, such as dehydrated placental tissue and micronized placental tissue. The term "placental tissue" as used herein does not include any of the components found in an umbilical cord, (e.g., Native Wharton's Jelly, umbilical cord vein and artery, and surrounding amniotic membrane.

The term "about" when used before a numerical value is inclusive of the stated value and has the meaning dictated by the context (e.g., includes the degree of error associated with measurement of the particular quantity, such as ±5%, ±1%, and ±0.2%).

The term "dehydrated" when defining a substance, such as micronized Native Wharton's Jelly, amnion, chorion, and the like, means that the substance has a water content of no more than about 10%, no more than about 5%, no more than about 1%, no more than about 0.5%, no more than about 0.2%, no more than about 0.1%, or no more than about 0.01%, or is free of any water. The term "dehydrate" or "dry", "dried" or any grammatical equivalent means to substantially remove water (e.g., to remove at least about 85%, about 90%, about 95%, about 99%, about 99.5%, about 99.8%, about 99.9% or about 99.99% of the water content in the substance) or to completely remove water from a substance to produce a dehydrated substance free of any water content.

The term "treatment" or "treating", to the extent it relates to a disease or condition, includes preventing the disease or condition from occurring, inhibiting the disease or condition, eliminating the disease or condition, and/or relieving one or more symptoms of the disease or condition.

Abbreviations

The following abbreviations when used throughout the specification and the appended claims, have the following meanings:

° C.=degrees Celsius
cc=cubic centimeter
cm=centimeter
Da=Dalton
DI=de-ionized
DMSO=dimethyl sulfoxide
EDTA=ethylenediaminetetraacetic acid
M=molar concentration (mol/L)
mg=milligram
mL=milliliter
mm=millimeter
PBS=phosphate buffered saline
rpm=rounds per minute
µm=micrometer Titles or subtitles may be used in the specification for the convenience of a reader, which are not intended to influence the scope of the present invention. Additionally, some terms used in this specification are more specifically defined below.

I. Native Wharton's Jelly

The umbilical cord (also called the navel string, birth cord or funiculus umbilicalis) is a conduit between the developing embryo or fetus and the placenta. During prenatal development, the umbilical cord is physiologically and genetically part of the fetus and, in humans, normally contains two arteries (the umbilical arteries) and one vein (the umbilical vein), surrounded by Native Wharton's Jelly. The outer layer of the umbilical cord is sheathed in amniotic membrane.

According to the present invention, Native Wharton's Jelly can be obtained from the umbilical cord of mammals such as humans, domestic animals such as cows, pigs, horses, dogs, cats, rabbits, rats and mice, and non-domesticated animals. Native Wharton's Jelly contains high amounts of host extracellular matrix (ECM) components (including chondroitin sulfate, collagen, hyaluronic acid (HA), proteoglycans, and stem cells. Native Wharton's Jelly may also include growth factors such as, for example, fibroblast growth factor (FGF), insulin-like growth factor I (IGF-I), transforming growth factor beta (TGF-beta), platelet-derived growth factor (PDGF) and epidermal growth factor (EGF). Native Wharton's Jelly also has a significant elasticity characteristic as well as binding of water molecules.

According to the present invention, Native Wharton's Jelly is collected through the gross processing of umbilical cord as described in greater detail below. The collected Native Wharton's Jelly is then dehydrated, followed by micronization, as described in greater detail below.

Umbilical Cord Tissue Collection

In the case of humans, the recovery or collection of umbilical cord tissue can be achieved, for example, in a hospital, where it is preferably collected during a Cesarean section birth. The donor, referring to the mother who is about to give birth, voluntarily submits to a comprehensive screening process designed to provide safe tissue for medical use. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), cytomegalovirus (CMV), and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the tissue, as will be appreciated by those skilled in the art.

Based upon a review of the donor's information and screening test results, the donor will either be deemed acceptable or not. In addition, at the time of delivery, cultures are taken to determine the presence of bacteria such as, for example, *Clostridium* or *Streptococcus*. If the donor's information, screening tests, and the delivery cultures are all satisfactory (i.e., do not indicate any risks or indicate acceptable level of risk), the donor is approved by a medical professional and the tissue specimen is designated as initially eligible for further processing and evaluation.

The umbilical cord tissue that is dissected off the placental disc during standard process and meets the above selection criteria can be processed immediately in accordance with the present invention, or it can be stored in a reservoir such as in a sterile shipment bag or container containing saline solution, which is then stored in a wet ice environment for shipment to a processing location or laboratory for processing in accordance with the present invention.

Gross Umbilical Cord Tissue Processing

An umbilical cord that is dissected from the placental disc as described above is first processed by making an incision along the umbilical cord at a depth of about 2 mm to about 3 mm, to thereby expose the arteries, veins and Native Wharton's Jelly. As would be understood by a person of ordinary skill in the art, the depth of the incision may of course vary depending upon the diameter or thickness of the dissected umbilical cord. The umbilical cord arteries and veins are then removed by utilizing, for example, undermining dissection techniques known in the art, with care given to maintain as much of the Native Wharton's Jelly as possible, to thereby provide umbilical cord tissue comprising Native Wharton's Jelly and umbilical cord amniotic membrane (hereinafter referred to as 'Umbilical Cord Tissue'). To increase the dissection and recovery of Native Wharton's Jelly from the Umbilical Cord Tissue, the umbilical cord may be cut into smaller sections, such as for example umbilical cord sections of about 4 cm to about 10 cm in length It is to be understood that, according to the present invention, the Umbilical Cord Tissue may or may not include amniotic membrane. For example, in certain aspects of the present invention, the Native Wharton's Jelly can be further isolated from the Umbilical Cord Tissue by dissecting the amniotic membrane from the Native Wharton's Jelly to thereby provide Native Wharton's Jelly free on any umbilical cord components (hereinafter referred to as "Isolated Wharton's Jelly"). The Isolated Wharton's Jelly can be, for example, further cut into strips of about 1 cm to about 4 cm by about 10 cm to about 30 cm, with a thickness of about 1.25 cm, although, other thicknesses are possible depending on the desired application.

According to the present invention, Umbilical Cord Tissue, or Isolated Wharton's Jelly, is rinsed and cleaned according to the standard Purion® process wash and rinse step as described in "PURION® Processed Dehydrated Human Amnion/Chorion Membrane Allografts", 2012, available at http://www.iopinc.com/wp-content/uploads/2012/05/Ambio_AM_Process_Monograph-May-12.pdf.
For example, Dehydration Unless otherwise indicated herein, the dehydration steps described herein can be employed for dehydration of Umbilical Cord Tissue or Isolated Wharton's Jelly. Accordingly, reference to dehydration of Umbilical Cord Tissue is intended to include, and may be referred to interchangeably with, Isolated Wharton's Jelly, unless otherwise indicated. After the washing and rinsing steps described above are completed, the Umbilical Cord Tissue can be dehydrated according to techniques described in greater detail below or as otherwise known in the art. In one aspect, Umbilical Cord Tissue can be placed onto a drying board. Exemplary drying boards include those described in, for example, U.S. Patent Application Publication No. US2014/0106447. In the case of Umbilical Cord Tissue that includes an intact amniotic membrane, the Umbilical Cord Tissue is place on the drying board with the Native Wharton's Jelly side facing upwards. The Umbilical Cord Tissue is then dried according to dehydration specifications described herein or as may be otherwise known in the art. For example, the Umbilical Cord Tissue can be dehydrated to substantially remove water from the Umbilical Cord Tissue (i.e., greater than about 90%, greater than about 95%, or greater than about 99%, of water present in the tissue is removed), or can be dehydrated to completely remove all water present in the Umbilical Cord Tissue (i.e., 100% of the water present in the Umbilical Cord Tissue is removed).

In one aspect, the Umbilical Cord Tissue is dehydrated by chemical dehydration followed by freeze-drying. For example, the chemical dehydration step is performed by contacting the Umbilical Cord Tissue with a polar organic solvent for a sufficient time and amount. The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the Umbilical Cord Tissue is contacted with a polar organic solvent at room temperature. No additional steps are required, and the Umbilical Cord Tissue can be freeze-dried directly as described below.

After dehydration, the Umbilical Cord Tissue can be freeze-dried in order to remove any residual water and polar organic solvent. In one aspect, the Umbilical Cord Tissue can be laid on a suitable drying fixture prior to freeze-drying. The drying fixture is preferably sized to be large enough to fully receive the Umbilical Cord Tissue, in a laid out, flat fashion. In one aspect, the drying fixture is made of Teflon® or of Delrin®, which is the brand name for an acetal resin engineering plastic sold by DuPont and which is also available commercially from Werner Machine, Inc. Marietta, Ga. Any other suitable material that is heat and cut resistant, capable of being formed into an appropriate shape to receive wet Umbilical Cord Tissue, can also be used for the drying fixture.

Once the Umbilical Cord Tissue is placed on the drying fixture, the drying fixture is placed in a freeze-dryer. The use of a freeze-dryer to dehydrate the Umbilical Cord Tissue can be more efficient and thorough as compared to other techniques such as thermal dehydration. In some embodiments, it is desirable to avoid ice crystal formation in the Umbilical Cord Tissue as this may damage the extracellular matrix in the Umbilical Cord Tissue. By chemically dehydrating the Umbilical Cord Tissue prior to freeze-drying, the formation of ice crystals and damage to the extracellular matrix can be avoided.

In another aspect, the dehydration step involves applying heat to the Umbilical Cord Tissue. For example, the Umbilical Cord Tissue is laid on a suitable drying fixture or board as described above, and the drying fixture is placed in a sterile Tyvex (or similar, breathable, heat-resistant, and sealable material) dehydration bag and sealed. The breathable dehydration bag prevents the Umbilical Cord Tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator, that has been preheated to about 35° C. to about 50° C., for between about 30 to about 120 minutes. In one aspect, the heating step can be performed for about 45 minutes at a temperature of about 45° C. to dry the Umbilical Cord Tissue sufficiently while at the same time without over-drying or burning the umbilical cord tissue. The specific temperature and time for any specific oven should be calibrated and adjusted based on other factors such as altitude, size of the oven, accuracy of the oven temperature, material used for the drying fixture, number of drying fixtures being dried simultaneously, whether a single or multiple frames of drying fixtures are dried simultaneously, and the like considerations.

While the dehydration of Umbilical Cord Tissue may be achieved by using dehydration devices known in the art, an innovative dehydration device which enhances the rate and uniformity of the dehydration process as described in U.S. Patent Application Publication No. US2014/0051059, which is incorporated herein by reference in its entirety, may be utilized. For example, in one embodiment, the drying time can be accelerated by up to about 40% in one configuration of such dehydration device in comparison to conventional drying ovens. In certain aspects of this embodiment, the Umbilical Cord Tissue is placed onto a drying fixture described herein and the drying fixture with the Umbilical Cord Tissue is inserted into the dehydration device for performing the dehydration process. In other aspects, multiple Umbilical Cord Tissues can be placed onto the drying fixture to simultaneously dry more than one Umbilical Cord Tissue in the dehydration device.

Preparation of Micronized Wharton's Jelly

After dehydrating the Native Wharton's Jelly or Umbilical Cord Tissue as described in detail above or as may otherwise be known in the art (collectively or individually, "Dehydrated Tissue"), the Dehydrated Tissue is micronized in accordance with the present invention to form a particle distribution comprising particles of one or more sizes (hereinafter referred to as "Micronized Wharton's Jelly"). For example, the Dehydrated Tissue can be cut into sections of about 2 cm by about 2 cm and prepared for micronization. The micronization can be achieved using instruments known in the art. For example, the Retsch Oscillating Mill MM400 (manufactured by and available from Retsch GmbH, Retsch-Allee 1-5, 42781 Haan, Germany) can be used to produce the Micronized Wharton's Jelly described herein.

In one aspect, the Micronized Wharton's Jelly is prepared by mechanical grinding or shredding of the Dehydrated Tissue.

In another aspect, Micronized Wharton's Jelly is prepared by cryogenic grinding of the Dehydrated Tissue. In this aspect, a grinding jar containing the Dehydrated Tissue is continually cooled with liquid nitrogen from an integrated cooling system before and during the grinding process. Thus, the sample is embrittled and volatile components are preserved. Moreover, the denaturing of proteins in the Dehydrated Tissue is minimized or prevented. For example, in one aspect, a CryoMill manufactured by and available from Retsch GmbH can be used.

For example, Dehydrated Tissue described herein can be placed in vials and the vials are subsequently sealed. The vials are placed in a Cryo-block, and the Cryo-block is placed in a Cryo-rack, each of which are manufactured by and available from Retsch GmbH. The Cryo-rack is placed into a liquid nitrogen holding-Dewar flask. The Dehydrated Tissue is subjected to vapor phase cooling for no more than about 30 minutes to about 60 minutes. The Cryo-rack is removed from the Dewar flask, and the Cryo-block is removed from the Cryo-rack. The Cryo-block is placed into a grinder (for example, SPEX Sample Prep GenoGrinder 2010, manufactured and available from SPEX SamplePrep, 65 Liberty St., Metuchen, N.J. 08840) and set at about 1,500 rpm for about 20 minutes. After about 20 minutes has elapsed, the Micronized Wharton's Jelly is inspected to ensure micronization in accordance with the particle size specifications of the present invention as described in greater detail below. If necessary, the Micronized Wharton's Jelly may be returned to the Dewar flask for an additional period of time, such as for example about 30 minutes to about 60 minutes, and then placed in the grinder for an additional period of time, such as for example about 20 minutes, to ensure sufficient micronization and desired particle size distribution as described in greater detail below.

Separation of Micronized Wharton's Jelly particles by respective sizes can be achieved by fractionation of the Micronized Wharton's Jelly in sterile water by forming a suspension of particles therein. According to such fractionation technique, the upper most portion of the suspension will contain predominantly the smallest particles and the lower most portion of the suspension will contain predominantly the heaviest particles. Fractionation leads to particle size separation and repeated fractionation will lead to separation of the micronized particles into varying sizes. The separated Micronized Wharton's Jelly particles can then be recombined in the desired ratio of particle size as is most appropriate for an intended use.

In another embodiment, separation is achieved utilizing one or more sieves having desired hole or pore sizes to achieve a desired particle size distribution in accordance with the present invention. For example, once the Micronized Wharton's Jelly is prepared as described above, it can be sorted by particle size using a series of sieves meeting the standards and specifications of the American Society for Testing and Materials (ASTM) s. For example, in some embodiments, sieves have respective hole or pore sizes of 355 µm, 300 µm, 250 µm, 150 µm, and 125 µm. The Micronized Wharton's Jelly is then sequentially transferred to the 355 µm sieve, followed by the 300 µm sieve, followed by the 250 µm sieve, followed by the 150 µm sieve, and followed by the 125 µm sieve. Prior to transfer of the Micronized Wharton's Jelly to a subsequent sieve, the respective sieve is agitated individually in order to thoroughly separate by size the Micronized Wharton's Jelly particles. In this example, once the Micronized Wharton's Jelly particles are effectively separated using the sieves, the Micronized Wharton's Jelly particles having particle sizes of 355 µm, 300 µm, 250 µm, 150 µm, and 125 µm are collected in separate labeled vials.

The particle size of the Micronized Wharton's Jelly can vary as well depending upon the application. It is to be understood that the term "micronized" is meant to include micron and sub-micron sized particles. In one aspect, the Micronized Wharton's Jelly has particles that are at or less than about 500 µm, at or less than about 400 µm, at or less than about 300 µm, at or less than about 200 µm, at or less than about 100 µm, at or less than about 75 µm, at or less than about 50 µm, at or less than about 25 µm, at or less than about 20 µm, at or less than about 15 µm, at or less than about 10 µm, at or less than about 9 µm, at or less than about 8 µm, at or less than about 7 µm, at or less than about 6 µm, at or less than about 5 µm, at or less than about 4 µm, at or less than about 3 µm, at or less than about 2 µm, or from about 2 µm to about 400 µm, from about 25 µm to about 300 µm, from about 25 µm to about 200 µm, or from about 25 µm to about 150 µm, or any range between any of the two numbers. In one aspect, the Micronized Wharton's Jelly has particles that have a diameter of less than about 150 µm, less than about 100 µm, or less than about 50 µm. In other aspects, particles having a larger diameter (e.g., about 150 µm to about 350 µm) are desirable. In other aspects, the particles have a diameter of about 25 µm to about 75 µm. In all cases, the diameter of the particle is measured along its longest axis.

In some embodiments, the Micronized Wharton's Jelly has a desired particle size distribution such that, for example, smaller sized particles may provide an immediate or short-term effect and larger particles may provide a prolonged or sustained long term effect. For example, in some embodiments, the Micronized Wharton's Jelly is a composition comprising multiple particle sizes such that, for example about 50% of the particles have a diameter of less than about 40 µM, about 25% of the particles have a diameter of from about 40 µm to less than about 60 µm, and about 25% of the particles have a diameter of more than about 60 µM. In other embodiments, about 25% of the particles have a diameter of less than about 40 µM, about 25% of the Micronized Wharton's Jelly particles have a diameter of from about 40 µM to less than about 60 µM, and about 50% of the particles have a diameter of more than about 60 µM.

In one embodiment, the surface area to volume ratio of the particles (based on a particle having a range of diameters as described above) is between the range of about 0.06 $\mu m^{-1}$ to about $6\times10^4$ $\mu m^{-1}$, about 0.06 $\mu m^{-1}$ to about $6\times10^3$ about 0.06 $\mu m^{-1}$ to about $6\times10^2$ $\mu m^{-1}$, or about 0.6 $\mu m^{-1}$ to about $6\times10^2$ $\mu m^{-1}$.

In one aspect, the Micronized Wharton's Jelly is substantially free of any placental tissue or a component thereof. Substantially free as used herein means that the Micronized Wharton's Jelly contains no more than about 10%, 5%, or 1% of placental tissue or a component thereof. In one aspect, the Micronized Wharton's Jelly is free of any placental tissue or a component thereof.

As would be appreciated by one skilled in the art, the particle size of the Micronized Wharton's Jelly can be reduced to nano-range, thereby significantly increasing the density of the Micronized Wharton's Jelly particles and improving the release rate of the Micronized Wharton's Jelly particles upon application to a treatment site. For example, the Micronized Wharton's Jelly can be subjected to conventional methods known in the art, including differential centrifugation, thereby reducing the particle size to nano-range. Particle size reduction using a suitable technology or device is within the purview of one skilled in the art.

II. Micronized Wharton's Jelly Compositions

According to yet another aspect of the present invention, compositions and formulations comprising Micronized Wharton's Jelly are provided.

As described above, Native Wharton's jelly is a viscous gelatinous material that is difficult to deliver into the body for repair and/or regeneration. According to the present invention, the Micronized Wharton's Jelly, and compositions and formulations thereof, can be readily and reliably delivered to the injured region of a subject for repair and/or regeneration of the articular surface cartilage thereof. In one aspect, the present invention provides Micronized Wharton's Jelly and compositions thereof having a controlled viscosity such that when delivered to the injured region of a subject, it remains substantially localized for the repair and/or regeneration thereof. As described in greater detail below, Micronized Wharton's Jelly according to the present invention can be suspended in a pharmaceutically acceptable aqueous carrier, such as saline, sterile water, or any suitable buffer known in the art, to form a suspension or a gelatinous gel composition, that can be in the form of a liquid, gel, or paste suitable for delivery into the space adjacent the articular surface cartilage injured region of a subject as described herein. As such, the Micronized Wharton's Jelly disclosed herein is versatile because when employed at sufficient concentrations, it can be hydrated into a gel or paste and administered topically, or it can be injected into the body through the use of a needle and syringe. In at least these respects, Micronized Wharton's Jelly according to the present invention, or compositions or formulations thereof, can be delivered in a manner that is more convenient than Native Wharton's jelly.

In one aspect, the Micronized Wharton's Jelly described herein can be formulated in any excipient the biological system or entity can tolerate to produce compositions or formulations for the administration of the Micronized Wharton's Jelly to a subject. Examples of aqueous excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as carboxymethylcellulose or salts thereof, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. Additionally, the compositions or formulations for the administration of the Micronized Wharton's Jelly to a subject can include carriers, thickeners, diluents, preservatives, surface active agents and the like in addition to the Micronized Wharton's Jelly described herein.

In some embodiments, the composition further comprises micronized placenta tissue or a component thereof, such as micronized placental amnion, as described in International Patent Application WO 2012/112410, as well as in U.S. provisional application Ser. Nos. 61/442,346, 61/543,995, and 61/683,700. The contents of these applications are specifically incorporated herein by reference in their entireties. In such embodiments, the micronized placenta tissue or component thereof can be added prior to and/or following micronization, and/or prior to and/or following dehydrating the Native Wharton's Jelly or Umbilical Cord Tissue as described in detail above.

In another aspect, placental tissue, or a component thereof, such as amnion, the intermediate tissue layer, chorion, and additional components, can be added prior to and/or following micronization, and/or prior to and/or following dehydrating the Native Wharton's Jelly or Umbilical Cord Tissue as described in detail above.

In one aspect, a filler can be added prior to and/or following micronization, and/or prior to and/or following dehydrating the Native Wharton's Jelly or Umbilical Cord Tissue as described in detail above. Examples of fillers include, but are not limited to, allograft pericardium, allograft acellular dermis, purified xenograft Type-1 collagen, biocellulose polymers or copolymers, biocompatible synthetic polymer or copolymer films, purified small intestinal submucosa, bladder acellular matrix, cadaveric fascia, or any combination thereof.

In another aspect, a bioactive agent can be added prior to and/or following micronization, and/or prior to and/or following dehydrating the Native Wharton's Jelly or Umbilical Cord Tissue as described in detail above. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon administration of the Micronized Wharton's Jelly with bioactive agent to the region of interest on a subject, the bioactive agent is delivered to the region over a period of time. Thus, the Micronized Wharton's Jelly or a composition thereof as described herein is a useful delivery vehicle for bioactive agents and other pharmaceutical agents when administered to a subject. As would be understood by one skilled in the art, release profiles of the bioactive agents from the Micronized Wharton's Jelly composition as described herein can be modified based on, among other things, the selection of the components comprising the Micronized Wharton's Jelly composition as well as the size of the particles.

The compositions or formulations for the administration of the Micronized Wharton's Jelly to a subject can be prepared using techniques known in the art. In one aspect, compositions or formulations are prepared by admixing Micronized Wharton's Jelly described herein with a pharmaceutically-acceptable compound and/or carrier.

It will be appreciated that the amount of Micronized Wharton's Jelly in a specified composition will vary according to the size of the particles in the Micronized Wharton's Jelly being utilized, the particular compositions formulated, the mode of application or delivery, and the particular situs or region and subject being treated. Dosages for a given subject can be determined using conventional considerations. For example, physicians and formulators, skilled in the art of determining doses and/or dosing regimens of the compositions or formulations for the administration of the Micronized Wharton's Jelly to a subject, can to determine the appropriate dose or dosing regimen according to standard recommendations (Physician's Desk Reference, Barnhart Publishing (1999)).

In some embodiments, the Micronized Wharton's Jelly can be suspended in a pharmaceutically acceptable aqueous carrier, such as saline, sterile water, or any suitable buffer known in the art to form a suspension or a gelatinous gel composition. The composition can thus be in the form of a liquid, gel, or paste.

In some embodiments, sterile water is used to create a flowable gel composition comprising Micronized Wharton's Jelly that is suitable for injection with a syringe and needle while maintaining a controlled viscosity of such flowable gel composition such that when delivered to the injured region of a subject, it remains substantially localized with little or no migration out of the injured region for the repair and/or regeneration thereof. For example, about 0.1 to about 1 g (such as about 0.5 g) of Micronized Wharton's Jelly can be mixed with about 1 mL to about 2 mL (such as about 1.3-1.4 mL) of water to provide a flowable gel material. In some embodiments, the concentration of the Micronized Wharton's Jelly in the composition is about 0.05 g/mL to about 1 g/mL, such as about 0.05 g/mL, about 0.1 g/mL, about 0.2 g/mL, about 0.3 g/mL, about 0.4 g/mL, about 0.5 g/mL, about 0.6 g/mL, about 0.7 g/mL, about 0.8 g/mL, about 0.9 g/mL, about 1 g/mL, or any ranges between any two values, including the end points. The material is in a smooth consistency that is able to be loaded into a syringe and pass through a needle, such as a 25-27 gauge needle, wherein the viscosity of the flowable gel remains substantially unchanged.

In some embodiments, droplets of the flowable gel as described above is applied onto a surface, such as a smooth and non-embossed surface of a board, and allowed to dry substantially or completely. In some embodiments, the diameter of droplets are about 5 to about 1 mm, such as about 2.5 mm. After drying, solid pellets form with minimum reduction in overall diameter. In some embodiments, the solid pellets are in a circular shape/configuration. As used herein, substantially means that the dried pellets comprises no more than about 10%, about 5%, about 2%, about 1%, about 0.5% or about 0.1% residue water.

The pellets can be placed in sterile water to re-hydrate. In some embodiments the rehydration time is about or more than about 1 hour. In some embodiments, the diameter of the pellets increases after rehydration. In some embodiments, the diameter increases by about 1.1 to about 3 fold, such as about 1.5 to about 2.5 fold or about 2 fold. In some embodiments, there is no indication of loss of integrity in size or shape in aqueous condition for an extended period, such as more than about 24 hours.

In some embodiments, the Micronized Wharton's Jelly is compressed into a mold having a desired shape or size to form a molded Micronized Wharton's Jelly that takes the shape and size of the mold and exhibits a desired cohesiveness and density. It is within the purview of one of ordinary skill in the art to select suitable molding material, such as silicone, resin, Teflon®, or stainless steel, to form a mold of desired shape and size.

The compositions or formulations for the administration of the Micronized Wharton's Jelly to a subject described herein can be administered in a number of ways depending on whether local or systemic treatment is desired, and on the area to be treated. In one aspect, administration can be by injection, where the composition is formulated into a liquid or gel. In other aspects, the composition can be formulated to be applied internally to a subject. In other aspects, the composition can be applied topically (including ophthalmically, vaginally, rectally, intranasally, orally, or directly to the skin).

In one aspect, the compositions of Micronized Wharton's Jelly can be formulated as a topical composition applied directly to the skin. Formulations for topical administration can include, emulsions, creams, aqueous solutions, oils, ointments, pastes, gels, lotions, milks, foams, suspensions and powders. In one aspect, the topical composition can include one or more surfactants and/or emulsifiers. Topical application of Micronized Wharton's Jelly is particularly well suited for the treatment of burns, psoriatic sores, dermatitis, wrinkles, and the like.

Micronized Wharton's Jelly compositions described herein can further comprise a surfactant (or surface-active substances) or emulsifier.

The surfactants may be anionic, non-ionic, cationic and/or amphoteric surfactants. Typical examples of anionic surfactants include, but are not limited to, soaps, alkylbenzenesulfonates, alkanesulfonates, olefin sulfonates, alkyl ether sulfonates, glycerol ether sulfonates, alpha-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. Examples of non-ionic surfactants include, but are not limited to, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. Examples of amphoteric or zwitterionic surfactants include, but are not limited to, alkylbetaines, alkylamidobetaines, aminopropionates, aminoglycinates, imidazolinium-betaines and sulfobetaines.

In one aspect, the surfactant can be fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, alpha-olefinsulfonates, ether carboxylic acids, alkyl oligoglucosides, fatty acid glucamides, alkylamidobetaines, amphoacetals and/or protein fatty acid condensates.

Examples of zwitterionic surfactants include betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate.

In one aspect, the emulsifier can be a nonionogenic surfactant selected from the following: addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical; alkyl and/or alkenyl oligoglycosides having 8 to 22 carbon atoms in the alk(en)yl radical and the ethoxylated analogs thereof; addition products of from 1 to 15 mol of ethylene oxide onto castor oil and/or hydrogenated castor oil; addition products of from 15 to 60 mol of ethylene oxide onto castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide; partial esters of polyglycerol (average degree of self-condensation 2 to 8), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide; mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof; wool wax alcohols; polysiloxane-polyalkyl-polyether copolymers and corresponding derivatives; and block copolymers, e.g. polyethylene glycol-30 dipolyhydroxystearates. In one aspect, the emulsifier is a polyalkylene glycol such as, for example, polyethylene glycol or polypropylene glycol. In another aspect, the emulsifier is polyethylene glycol having a molecular weight 100 Da to 5,000 Da, 200 Da to 2,500 Da, 300 Da to 1,000 Da, 400 Da to 750 Da, 550 Da to 650 Da, or about 600 Da.

In another aspect, the emulsifier is a poloxamer. In one aspect, the poloxamer is a nonionic triblock copolymer composed of a central hydrophobic chain of polyoxypropylene (e.g., (poly(propylene oxide)) flanked by two hydrophilic chains of polyoxyethylene (e.g., poly(ethylene oxide)). In one aspect, poloxamer has the formula

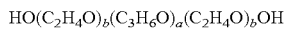

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the tradename Pluronic® manufactured by BASF. Non-limiting examples of poloxamers useful herein include, but are not limited to, Pluronic® F68, P103, P105, P123, F127, and L121.

In another aspect, the emulsifier is composed of one or more fatty alcohols. In one aspect, the fatty alcohol is a liner or branched $C_6$ to $C_{35}$ fatty alcohol. Examples of fatty alcohols include, but are not limited to, capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z,12Z-octadecadien-1-ol), elaidolinoleyl alcohol (9E,12E-octadecadien-1-ol), linolenyl alcohol (9Z,12Z,15Z-octadecatrien-1-ol) elaidolinolenyl alcohol (9E,12E,15-E-octadecatrien-1-ol), ricinoleyl alcohol (12-hydroxy-9-octadecen-1-ol), nonadecyl alcohol (1-nonadecanol), arachidyl alcohol (1-eicosanol), heneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), montanyl alcohol, cluytyl alcohol (1-octacosanol), myricyl alcohol, melissyl alcohol (1-triacontanol), geddyl alcohol (1-tetratriacontanol), or cetearyl alcohol.

In one aspect, the carrier used to produce the composition is a mixture polyethylene and one or more fatty alcohols. For example, the carrier is composed of 50% to 99% by weight, 75% to 99% by weight, 90% to 99% by weight, or about 95% by weight polyethylene glycol and 1% to 50% by weight, 1% to 25% by weight, 1% to 10% by weight, or about 5% by weight fatty alcohol. In a further aspect, the carrier is a mixture of polyethylene glycol and cetyl alcohol.

The Micronized Wharton's Jelly compositions can also include one or more additional components such as, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, swelling agents, insect repellents, hydrotropes, solubilizers, preservatives, perfume oils and dyes. Examples of each of these components are disclosed in U.S. Pat. No. 8,067,044, which is incorporated by reference with respect these components.

The Micronized Wharton's Jelly compositions described herein can be prepared by mixing the Micronized Wharton's Jelly with a carrier for a sufficient time such that the particles are substantially evenly dispersed throughout the carrier. In the case where the carrier is composed of two or more components, the components can be admixed with one another prior to the addition of the Micronized Wharton's Jelly. The amount of Micronized Wharton's Jelly present in the composition can vary depending upon the application. In one aspect, the Micronized Wharton's Jelly is from about 0.1% to about 99%, about 0.5% to about 90%, about 1% to about 75%, about 1% to about 50%, about 1% to about 20%, about 1% to about 10%, about 2% to about 5%, or about 3% by weight of the composition. Exemplary procedures for making Micronized Wharton's Jelly compositions described herein are provided in the Examples.

In addition to the advantages discussed above, the ability of the larger Micronized Wharton's Jelly particles to absorb fluids permits them to be admixed with a variety of substances (e.g., any of the bioactive agents described herein) to produce compositions or formulations for the administration of the Micronized Wharton's Jelly to a subject with enhanced activity. For example, the larger particles can be mixed with additional hemostatic agents, such as antifibrinolytics, vitamin K, fibrinogen, and blood coagulation factors, to enhance blood clotting at a wound. In other aspects, the larger particles can be admixed with autogeneous materials such as bone derived from the patient. Here the Micronized Wharton's Jelly can be administered directly to the periosteal interface. In other aspects, the larger micronized particles can be admixed with fibrin glues to enhance wound healing. Micronized Wharton's Jelly can enhance the ability of the fibrin glue to form fibrin clots and enhance tissue repair. Thus, the larger particles in combination with the fibrin glue can further reduce the need of sutures typically used to close wounds.

In one embodiment, the Micronized Wharton's Jelly can be embedded into the surface of the amnion or chorion which is to contact the tissue surface of a subject. Conventional technology such as high velocity sprayer can result in surface loading of the Micronized Wharton's Jelly so as to result in enhanced release rates of growth factors and the like into the tissue.

Plasticizers

In yet another aspect, the Micronized Wharton's Jelly composition components are admixed with at least one plasticizer. The terms "plasticizer" and "plasticizing agent" can be used interchangeably in the present invention. A plasticizing agent can include any agent or combination of agents that can be added to modify the mechanical properties of the composition or a product formed from the composition. One skilled in the art would select a suitable plasticizer based on the biocompatibility of the plasticizer, effect of plasticizer on the degradation or erosion rate of the Micronized Wharton's Jelly composition in vivo, effect of the plasticizer on the properties of the mixture to facilitate the molding/compression process, and/or effect of the plasticizer on the strength, flexibility, consistency, hydrophobicity and/or hydrophilicity of the composition. In some aspects, the plasticizer is dehydrated and/or micronized prior to being mixed with the Micronized Wharton's Jelly such that the mixture of plasticizer and Micronized Wharton's Jelly has a sufficiently low water content to permit compression in a non-porous mold.

Without intending to be bound by any theory or mechanism of action, plasticizers can be added, for example, to reduce crystallinity, lower the glass-transition temperature (Tg), or reduce the intermolecular forces between components within the composition, with a design goal that may include creating or enhancing a flow between components in the composition. The mechanical properties that are modified include, but are not limited to, Young's modulus, tensile strength, impact strength, tear strength, and strain-to-failure. A plasticizer can be monomeric, polymeric, co-polymeric, or a combination thereof, and can be added to a composition with or without covalent bonding. Plasticization and solubility are analogous to the extent that selecting a plasticizer involves considerations similar to the considerations in selecting a solvent such as, for example, polarity. Furthermore, plasticizers can also be added to a composition through covalent bonding that changes the molecular structure of the composition through copolymerization.

Examples of plasticizing agents include, but are not limited to, low molecular weight polymers such as, for example, single-block polymers, multi-block polymers, and copolymers; oligomers such as, for example, lactic acid oligomers including, but not limited to, ethyl-terminated oligomers of lactic acid; dimers of cyclic lactic acid and glycolic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; saturated and unsaturated fatty acids; fatty alcohols; cholesterol; steroids; phospholipids such as, for example, lecithin; proteins such as animal proteins and vegetable proteins; oils such as, for example, the vegetable oils and animal oils; silicones; acetylated monoglycerides; diglycerides; triglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, Methylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, methylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other embodiments, the plasticizers include, but are not limited to ethers and polyethers such as, for example, poly(alkylene glycols) such as poly(ethylene glycols) (PEG), poly(propylene glycols), and poly(ethylene/propylene glycols); PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other embodiments, the plasticizers include, but are not limited to, amides such as, for example, oleic amide, erucic amide, and palmitic amide; alkyl acetamides such as, for example, dimethyl acetamide; sulfoxides such as for example, dimethyl sulfoxide (DMSO); pyrrolidones such as, for example, n-methyl pyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In other embodiments, the plasticizers include, but are not limited to vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid; essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, chamomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and any analogs, derivatives, copolymers and combinations thereof.

It should be appreciated that, in some embodiments, one of skill in the art may select one or more particular plasticizing agents in order to exclude any one or any combination of the above-described plasticizing agents.

In some embodiments, the plasticizing agent can include a component that is water-soluble. In other embodiments, the plasticizing agent can be modified to be water-soluble. In some embodiments, the plasticizing agent can include a component that is lipid-soluble. In other embodiments, the plasticizing agent can be modified to be lipid-soluble. Any functional group can be added to modify the plasticizer's behavior in a solvent such as, for example, body fluids that are present in vivo.

Cross-Linking

In a further aspect, the potential in vivo degradation or erosion rate of Micronized Wharton's Jelly compositions formulations according to the present invention, as well as the density and cohesiveness of the Micronized Wharton's Jelly and other components, can be modified, for example, by cross-linking. The Micronized Wharton's Jelly can be cross-linked with other components, such as the amnion tissue, intermediate tissue layer, chorion, or a second amnion tissue. For example, a cross-linking agent can be added prior to and/or after micronization as described herein. In general, the cross-linking agent is nontoxic and non-immunogenic. When the components are treated with the cross-linking agent, the cross-linking agent can be the same or different. In one aspect, the Native Wharton's Jelly, Umbilical Cord Tissue (with or without Native Wharton's Jelly, and/or other components can be treated separately with a cross-linking agent or, in the alternative, Native Wharton's Jelly, Umbilical Cord Tissue (with or without Native Wharton's Jelly, and/or other components can be treated together with the same cross-linking agent. In certain aspects, Native Wharton's Jelly, Umbilical Cord Tissue (with or without Native Wharton's Jelly, and/or other components can be treated with two or more different cross-linking agents. The conditions for treating the Native Wharton's Jelly, Umbilical Cord Tissue (with or without Native Wharton's Jelly, and/or other components can vary. In other aspects, Micronized Wharton's Jelly can subsequently be treated with a cross-linking agent. In one aspect, the concentration of the cross-linking agent is from about 0.1 M to about 5 M, about 0.1 M to about 4 M, about 0.1 M to about 3 M, about 0.1 M to about 2 M, or about 0.1 M to about 1 M. Preferably, Native Wharton's Jelly, Umbilical Cord Tissue (with or without Native Wharton's Jelly, and/or other components are cross-linked prior to dehydration such that the cross-linked components have a sufficiently low water content to permit compression or molding in a non-porous mold.

In certain aspects, a molded Micronized Wharton's Jelly as described below can be treated with the cross-linking agent. Preferably, the composition is subjected to gas/fume cross-linking prior to compression and before or after micronization such that the water content of the composition is maintained at a low level, e.g., less than about 20%, less than about 15%, less than about 10%, or less than about 5%. The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehyde such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N[alpha-maleimidoacetoxy]succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and 1-ethyl-3-[3-dimethylaminopropyl]carbodiimide hydrochloride, a bifunctional oxirane (OXR), ethylene glycol diglycidyl ether (EGDE), nordihydroguaiaretic acid (NDGA).

In one aspect, sugar is the cross-linking agent, where the sugar can react with proteins present in the Native Wharton's Jelly, Umbilical Cord Tissue (with or without Native Wharton's Jelly, and/or other components to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as cross-linking agents include, but are not limited to, D-ribose, glycerose, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof.

Molded Compositions

In some embodiments, the Micronized Wharton's Jelly in the form of flowable gel material can be placed in a mold with an appropriate size and shape and allowed to dry in the mold to form a solid molded composition suitable for placing into, for example, a drill fracture of the articular cartilage. Accordingly, in one embodiment, a method is provided for producing a molded composition comprising Micronized Wharton's Jelly having a preselected disintegration rate in vivo. It is to be understood that altering particle size allows for predictable changes in the disintegration rate of the molded composition. According to one embodiment, the Micronized Wharton's Jelly is molded under pressure wherein the particle size is adjusted as described above prior to said molding so as to provide a molded composition having a preselected disintegration rate. In one embodiment, the disintegration rate in vivo can be reduced (slowed) by decreasing the particle size of the Micronized Wharton's Jelly.

In another aspect, altering one or more for the particle size of Micronized Wharton's Jelly, the compression force used, and the rate at which the compression force is applied allows for predictable changes in the stiffness and/or strength of the molded composition. Accordingly, further provided is a method for producing a molded Micronized Wharton's Jelly composition having a preselected strength and/or stiffness, said method comprising molding Micronized Wharton's Jelly under pressure wherein one or more of the above parameters is adjusted prior to said molding so as to provide a molded a composition having a preselected strength and/or stiffness. In one embodiment, the strength of the molded composition can be increased by decreasing the particle size of the Micronized Wharton's Jelly, while maintaining each of the other factors listed above. In one embodiment, the strength of the molded composition can be increased by increasing the compression force used. In one embodiment, the strength of the molded composition can be increased by decreasing the compression rate used.

The Micronized Wharton's Jelly, when subjected to pressure preferably in a non-porous mold, forms a desired shape and size defined by the mold. While a porous mold is less preferred, it is contemplated that such can be used in the methods of the present invention if water or other solvents are allowed to escape during molding.

The compression force, compression rate, and number of compression cycles can vary during the formation of the molded, Micronized Wharton's Jelly composition. In one aspect, the compression force used to mold the Micronized Wharton's Jelly is between about 10 Newtons and about 1000 Newtons. In another embodiment, the compression force used is between about 100 Newtons and about 400 Newtons. The compression force can vary based on the intended use. For example, a use requiring greater strength and/or stiffness of the molded composition will require a greater force.

In one aspect, the compression rate used to mold the Micronized Wharton's Jelly is between about 0.001 mm/sec and about 5 mm/sec. In another embodiment, the compression rate is between about 0.008 mm/sec and about 1.5 mm/sec. The compression rate can vary based on the intended use. For example, a use requiring greater strength and/or stiffness of the molded composition will require a slower rate.

The molded Micronized Wharton's Jelly composition has a sufficient density and cohesive mass to maintain its size and shape at least until the molded composition is introduced to a subject. The cohesion of the molded composition is determined, in part, by the particle size of the Micronized Wharton's Jelly. For example, Micronized Wharton's Jelly having larger particle size require higher compressive pressure and/or longer compression time to obtain a molded Micronized Wharton's Jelly composition having the same density as that of a molded Micronized Wharton's Jelly composition composed of dehydrated Micronized Wharton's Jelly having smaller particle size. In other words, for molded Micronized Wharton's Jelly compositions obtained under the same compression condition, the compositions having larger particle size have less density and dissociate at a higher rate in comparison to the compositions having smaller particle size.

The particle size of the Micronized Wharton's Jelly compositions also affects the release rate of the growth factors and other active molecules present in the composition. Without being bound by theory and with all other factors being equal, it is contemplated that smaller particle size creates a larger overall surface area of components within the composition. A larger surface area may result in an increased release of factors from the Micronized Wharton's Jelly, and/or a faster rate of release. Smaller particles are contemplated to allow for improved compressibility and increased strength. Molded, Micronized Wharton's Jelly compositions made with larger particles may disintegrate faster than those made with smaller particles. Therefore, the particle size of the Micronized Wharton's Jelly can be optimized, thereby obtaining the molded Micronized Wharton's Jelly composition having a desired cohesiveness, surface area, and desired end results when administered to a subject.

Optionally, one or more adhesives can be admixed with the Micronized Wharton's Jelly prior to being introduced into the mold. Examples of such adhesives include, but are not limited to, fibrin sealants, cyanoacrylates, gelatin and thrombin products, polyethylene glycol polymer, albumin, and glutaraldehyde products. The adhesives used in the process should be dehydrated prior to being mixed with the micronized amnion composition such that the mixture of adhesives and micronized amnion composition has a sufficiently low water content to permit compression in a non-porous mold.

In addition to Dehydrated Tissue as described above, additional dehydrated components such as amnion, the intermediate tissue layer, and/or chorion, can be added to the composition prior to and/or after micronization. In one aspect, dehydrated filler can be added. Examples of fillers include, but are not limited to, allograft pericardium, allograft acellular dermis, purified Type-1 collagen, biocellulose polymers or copolymers, biocompatible synthetic polymer or copolymer films, purified small intestinal submucosa, bladder acellular matrix, cadaveric fascia, bone particles (including cancellous and cortical bone particles), or any combination thereof.

In another aspect, a dehydrated bioactive agent can be added to the composition prior to and/or after micronization. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the molded, dehydrated Micronized Wharton's Jelly composition with bioactive agent to the region of interest, the bioactive agent is delivered to the region over time. Thus, the molded, dehydrated Micronized Wharton's Jelly compositions described herein are useful as delivery vehicles of bioactive agents and other cosmetic agents when administered to a subject. Release profiles can be modified based on, among other things, the selection of the components used to make the molded composition as well as the size of the particles contained in the composition.

Injectable Compositions

In one aspect, provided Micronized Wharton's Jelly that is suitable for injection with a syringe and needle while maintaining a controlled viscosity of such flowable gel composition such that when delivered to the injured region of a subject, it remains substantially localized with little or no migration out of the injured region for the repair and/or regeneration thereof. In preferred embodiments, the injectable composition is a gel. Aqueous forms of the Micronized Wharton's Jelly compositions generally form a gel, but these gels may further include gel-forming pharmaceutically acceptable polymers such as gelatin, methylcellulose and polyethylene glycol.

It is contemplated that the injectable gels of Micronized Wharton's Jelly disclosed herein can been used as vehicles for the treatment of patients to sustain the in vivo release of biologically active compounds found in Native Wharton's Jelly. While the diffusion of biologically active compounds through Native Wharton's Jelly is hindered by the viscosity of these systems as well as the tortuous diffusion path that results from the three dimensional polymeric network that is present, such hindrances are overcome by the Micronized Wharton's Jelly formulations and compositions of the present invention.

The injectable gels of Micronized Wharton's Jelly may include one or more of an osmotic agent, hydrophobic agent, and surface active agent. Osmotic agents increase the rate of water sorption into the gel and provide an increase in the rate of release of the biologically active compounds found in Native Wharton's Jelly. Any conventional osmotic agents may be used in accordance with the invention. Preferred osmotic agents include mannitol, dextrose, and sodium chloride. Hydrophobic agents reduce the rate of elimination of the gel from the injection site and decrease the rate of release of the biologically active compounds found in Native Wharton's Jelly. Any conventional hydrophobic agents may be used in accordance with the invention. Preferred hydrophobic agents include cholesterol and cholesterol derivatives such as cholesterol sulfate, cholesterol acetate and cholesterol hemisuccinate. Surface active agents increase the rate of elimination of the gel from the injection site and provide an initially high rate of release of the biologically active compounds found in Wharton's jelly. Any conventional surface active agents may be used in accordance with the invention. Preferred surface active agents are stearic acid, palmitic acid, $C_6$-$C_{26}$ carboxylic acids, and the salts of these acids. Other surface active agents include polyoxyethylene glycols (e.g., PLURONIC's) and polyoxyethylene sorbitan mono-oleates (e.g., POLYSORBATE's).

In some embodiments, the injectable gel comprising Micronized Wharton's Jelly can be used to treat a patient by injecting the gel into the patient to both repair and regenerate the patient's articular surface cartilage.

In further embodiments, the injectable comprising Micronized Wharton's Jelly can be used to treat a patient by injecting the gel into the synovial joints of a patient. Synovial fluid is responsable for the operation and protection of the joints. Synovial fluid has visoelastic properties that lubricate the joint and absorb shock. However, in degenerative knee osteoarthritis for example, the synovial fluid degrades and ceases to protect the joint.

Viscosupplementation therapy involves injecting a gel into the joint to replace faulty synovial fluid. Viscosupplementation can reduce or eliminate pain and help restore joint mobility. Viscosupplementation products currently on the market are gels that contain hyaluronic acid. However, the persistence of gels based on hyaluronic acid is low in a joint (hours to days) because the hyaluronic acid readily degrades in vivo.

In contrast, it is contemplated that the injectable gels comprising Micronized Wharton's Jelly can persist at the site of injection, such as on an articular surface cartilage or at a synovial joint, from about 6 to about 12 hours, about 12 to about 14 hours, about 24 hours to about 36 hours, about 36 hours to about 48 hours, about 48 hours to about 60 hours, about 60 hours to about 100 hours or more.

III. Treatment of Articular Surface Defects

In another aspect, a method of treating an articular surface defect is provided.

Articular cartilage which serves as the lining of the joint has unique biochemical and physical qualities which confer nearly frictionless characteristics. Articular surface defects can be caused by both acute and repetitive trauma. A severe impact injury may cause injury to a focal area of an articular cartilage. Defects in the articular surface may lead to osteoarthrosis of the joint. Such defects can occur at joints of such as, shoulders, elbows, knees, hips, feet, ankles, hand and wrists, and the like. Three classes of chondral and osteochondral injuries can be identified based on the type of tissue damage and the repair response: (1) damage to the joint surface that does not cause visible mechanical disruption of the articular surface, but does cause chondral damage and may cause subchondral bone injury; (2) mechanical disruption of the articular surface limited to articular cartilage; and (3) mechanical disruption of articular cartilage and subchondral bone.

Articular surface defects can be graded based on the depth of the injury of articular cartilage. Grade I is when the cartilage has a soft spot or blisters, Grade II refers to minor tears visible in the cartilage, including fissuring or crater depth less than half the full thickness, Grade III refers to lesions have deep crevices (more than 50% of cartilage layer), including deep defects that are through most of the thickness of the cartilage, and the most severe, Grade IV refers to a full thickness defects with exposed bone.

Articular cartilage has poor healing qualities. An articular surface defect is difficult to heal or regenerate spontaneously. The approaches in addressing articular surface defects or articular cartilage defects typically involve "repair" and/or "regeneration". "Repair" refers to healing of the injured tissue or replacement by cell proliferation and new ECM. "Regeneration" refers to formation of entirely new articular surface, preferably identical to the original tissue.

Native Wharton's Jelly is rich in ECM comprising a variety of fibrous proteins, interstitial proteins, and signaling molecules, including glycosaminoglycans (GAGs), proteoglycans, and growth factors, including transforming growth factor beta 1 (TGF-β1), fibroblast growth factor (FGF), insulin-like growth factor I (IGF-I), platelet-derived growth factor (PDGF) and epidermal growth factor (EGF). Native Wharton's Jelly is a unique ECM further due to in part by its collagen types, including types I, II, III, IV, V, VI, and VII, and its ability to bind water within specific various layers. Native Wharton's Jelly also has a significant elasticity characteristic as well as binding of water molecules. It is contemplated that Native Wharton's Jelly will provide essential elements to both repair and regenerate articular surface cartilage. In some embodiments, growth factors are introduced to facilitate repair or regeneration. The growth factors can chemotactically cause cell proliferation, deliver ECM and direct cellular differentiation to hyaline cartilage formation rather than formation of the tough, dense, fibrous material fibrocartilage, which is not smooth and glassy, and not ideal for joints.

One of the most widely used surgical techniques for cartilage repair is the micro-fracture procedure. In this procedure, a disruption of the subchondral bone and cartilage is done in an attempt to induce bleeding and stimulate bone marrow stem cells. In larger defects, small amounts of subchondral bone maybe removed and mixed with various other bone material in an effort to promote healing. In this application, the Micronized Wharton's Jelly or a composition or formulation thereof can be added, such as to the autogenous bone tissue being removed, mixed and replaced into the defect. In some embodiments, the Micronized Wharton's Jelly in the form of dried pellets, as described herein, is added. In some embodiments, the dried pellets are press-fitted into a drill hole site. In some embodiments, the Micronized Wharton's Jelly in the form of flowable gel material as described herein is placed in a mold with an appropriate size and shape and allowed to dry in the mold to form a solid molded composition suitable for placing into the drill fracture of the articular cartilage. It is surprising that after drying, the solid molded composition has minimum reduction in size. This allows reliable design of the shape and size of the mold according to the shape and size of the drill fracture in order to produce a solid molded composition that fits well in the fracture. Further, it is surprising that the solid composition, either in a pellet form or a molded form, does not readily re-dissolve when placed in an aqueous environment. This allows the Micronized Wharton's Jelly composition to be maintained at the drill fracture site for an extended period of time (such as at least one day, one week, two week, one month, or until completion of repair or regeneration) to provide long term effect in assisting repair or regeneration of the articular surface cartilage.

In some embodiments, the Micronized Wharton's Jelly in the form of a flowable gel as described herein is injected directly into a drill fracture site.

In one aspect, the Micronized Wharton's Jelly compositions and formulations described herein are also useful in enhancing or improving wound healing. The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

IV. Use in Angioplasty

In still another aspect, provided is use of the gel composition comprising Micronized Wharton's Jelly in cardiovascular procedures, such as angioplasty, a minimally invasive revascularization procedure. In an angioplasty procedure, an empty and collapsed balloon on a guide wire, known as a balloon catheter, is passed into a narrowed location of an obstructed artery in order to widen it. The narrowed location of an artery is often obstructed as a result of atherosclerosis. When reaching the narrowed location, the balloon is inflated by, for example, applying water pressures. The balloon forces expansion of the inner white blood cell/clot plaque deposits and the surrounding muscular wall, opening up the blood vessel for improved flow. The balloon is then deflated and withdrawn. A stent is optionally inserted at the time of ballooning to ensure the vessel remains open.

However, recurrent stenosis (restenosis) can occur after such endovascular treatment of atherosclerotic lesions in the peripheral, cerebrovascular, and coronary circulation. It has been reported that up to 60% of the patients receiving percutaneous angioplasty experience restenosis within the first 12 months post-procedure. Vascular inflammation after balloon angioplasty or stent implantation has been identified as a main cause of the restenotic process. Martin Schillinger and Erich Minar, Restenosis After Percutaneous Angioplasty: The Role of Vascular Inflammation, Vasc Health Risk Manag., March 2005; 1(1):73-78. It is contemplated that Micronized Wharton's Jelly can be used in heart intervention procedures, such as angioplasty to reduce inflammation and formation of restenosis.

In some embodiments, the injectable gel composition described herein is injected directly to the angioplasty or surgical site, or around the angioplasty site to reduce inflammation, prevent restenosis and facilitate healing. In one embodiment, provided is a method of preventing or reducing restenosis in a patient having angioplasty and/or stent implantation, said method comprising administering an injectable composition comprising Micronized Wharton's Jelly approximate to the site of the angioplasty and/or stent implantation. In some embodiments, the injectable gel composition is injected into the tissue proximate to the vascular site to which the angioplasty is performed, at the time of the procedure, or before or after the procedure. For example, the injectable gel composition is injected to the outside of the blood vessel where angioplasty is performed and forms a coating of the relevant section of the blood vessel. The gel is contemplated to stay in place for an extended period of time and provide a continuous supply of anti-inflammatory molecules, such as growth factors, which can cross the blood vessel wall to the site of angioplasty to prevent and/or reduce inflammation and restenosis. In some embodiments, additional injectable gel composition is injected into the tissue proximate to the angioplasty site after the initial injection, such as one week, one month, two months, or six months, etc., after the initial injection. The injections can be made periodically, such as once a week, once a month, once two-months, etc.

In some embodiments, the balloon used in the angioplasty procedure is covered with the gel composition described herein and when the balloon is inflated, the gel composition is applied to the vessel wall, and remains on the vessel wall for a period of time to reduce inflammation and prevent restenosis. In some embodiments, the stent applied to the antioplasty site is covered with the gel composition described herein, which provides protection to the artery from inflammation and prevent restenosis when the stent is placed in the artery.

In some embodiments, the gel stays localized where it is placed for a period of time of from about 6 to about 12 hours, about 12 to about 14 hours, about 24 hours to about 36 hours, about 36 hours to about 48 hours, about 48 hours to about 60 hours, about 60 hours to about 100 hours or more.

The following Examples are for illustrative purposes only and should not be interpreted as limitations of the claimed invention.

EXAMPLES

1. Preparation of Umbilical Cord Tissue for Micronization

Umbilical Cord Tissue is obtained by dissecting the umbilical cord off the placental disc during the standard process known in the art. Dissection continues by performing a vertical incision along the cord segment which extends approximately 2-3 mm in depth. The umbilical cord arteries and veins are then removed via undermine dissection technique with care given to maintain as much Wharton's jelly tissue as possible. To maximize the dissection and recovery of Native Wharton's Jelly cord sections, the cord may be cut into smaller sections of 4-10 cm in length. Upon completion of the dissection, section of the cord may proceed with the standard Purion process wash and rinse step. After washing and rinses are completed, cord segments are then placed onto a drying board with the Native Wharton's Jelly side facing upwards. Cord sections are dried to standard drying time specifications. Cord sections are then cut into 2×2 cm sections and prepared for micronization.

2. Micronization of Umbilical Cord Tissue

The dehydrated Umbilical Cord Tissue obtained according to the procedure described in Example 1 is then micronized to provide Micronized Wharton's Jelly, with target particle sizes of 25 µm-75 µm.

3. Preparation of a Gel Composition of Micronized Wharton's Jelly

Sterile water was used to create a flowable gel configuration with the Micronized Wharton's jelly obtained in Example 2. To achieve a smooth consistency capable of passing through a 25-27 gauge needle, 1358.08 µL of water was added to 0.504 g of Micronized Wharton's Jelly. This yielded 2.5 mL of flowable gel material comprising Micronized Wharton's Jelly which can be loaded onto a 1.0 cc syringe.

4. Preparation of a Pellet Composition of Micronized Wharton's Jelly

A 1.0 cc syringe was loaded with the Micronized Wharton's Jelly gel formulation prepared according to Example 3. Following loading and using an open bore technique, droplets of Micronized Wharton's Jelly gel was placed onto a standard drying board (smooth side, non-embossed) such that the average droplet diameter was about 2.5 mm. Droplets were allowed to dry completely for about 8 hours.

After drying, the droplets were observed to become solid pellets and maintained a circular shape/configuration with minimum reduction in overall diameter.

The pellets were then placed in sterile water to re-hydrate. The overall diameter of the pellets was observed to increase by about 2-fold after rehydration. No indication of loss of integrity in size or shape in aqueous condition for more than 24 hours.

5. Clinical Application of Micronized Wharton's Jelly

One of the most widely used surgical techniques for cartilage repair is the "micro-fracture" procedure. In this procedure a disruption of the subchondral bone and cartilage is done in an attempt to induce bleeding and stimulate bone marrow stem cells. In larger defects, small amounts of subchondral bone maybe removed and mixed with various bone other material in an effort to promote healing. In this application, Micronized Wharton's Jelly pellets prepared according to Example 4 are added to the autogenous bone tissue being removed, mixed and replaced into the defect.

In the case of a micro-fracture, the Micronized Wharton's Jelly flowable gel material obtained according to Example 3 can be injected directly into the drill fracture sites or Micronized Wharton's Jelly pellets obtained according to Example 4 can be press-fitted into each drill hole site.

What is claimed:

1. A method for inducing hyaline cartilage formation in a patient in need thereof, said method comprising introducing a composition comprising Wharton's jelly including one or more growth factors found in Wharton's jelly into a joint of said patient, wherein said composition is substantially free of umbilical cord tissue.

2. The method of claim 1, wherein the growth factor is selected from the group consisting of fibroblast growth factor (FGF), insulin-like growth factor I (IGF-I), transforming growth factor beta (TGF-beta), platelet-derived growth factor (PDGF), and epidermal growth factor (EGF).

3. The method of claim 1, wherein the composition further comprises a pharmaceutically acceptable carrier.

4. The method of claim 3, wherein the pharmaceutically acceptable carrier is selected from the group consisting of water, saline, and phosphate buffered saline.

5. The method of claim 1, wherein the composition further comprises a surfactant or an emulsifier.

6. The method of claim 1, wherein the composition further comprises a plasticizer.

7. The method of claim 1, wherein the composition is injectable.

8. The method of claim 7, wherein the injectable composition further comprises one or more of an osmotic agent, a hydrophobic agent, and a surface active agent.

9. The method of claim 1, wherein the composition is a liquid, a gel or a paste.

10. The method of claim 1, wherein the composition further comprises a biocompatible polymer.

11. The method of claim 10, wherein the biocompatible polymer is a plasticizer.

12. The method of claim 11, wherein the plasticizer is cross-linked with a biocompatible cross-linking agent.

13. The method of claim 1, wherein the composition further comprises amniotic membrane of an umbilical cord.

14. The method of claim 1, wherein the composition is substantially free of amniotic membrane of an umbilical cord.

15. The method of claim 1, wherein said patient suffers from an articular surface defect.

16. The method of claim 15, wherein the articular surface defect is localized at a joint of shoulder, elbows, knee, hip, feet, ankle, hand, and/or wrist of said patient.

17. The method of claim 16, wherein the composition is administered to the site of the articular surface defect.

18. The method of claim 1, wherein the composition is administered to the patient during a micro-fracture procedure.

19. The method of claim 1, wherein the composition is administered to a drill fracture site during a micro-fracture procedure.

20. The method of claim 1, wherein the composition is added to an autogenous bone tissue.

21. The method of claim 1, wherein the composition is administered to a synovial joint of said patient.

22. The method of claim 1, wherein the Wharton's jelly is micronized.

* * * * *